United States Patent [19]
Keil et al.

[11] Patent Number: 5,386,075
[45] Date of Patent: Jan. 31, 1995

[54] PROCESS FOR SEPARATING ETHYLBENZENE AND STYRENE BY DISTILLATION

[75] Inventors: Thomas Keil, Bottrop; Wilhelm Hüwels; Georg Doll, both of Essen, all of Germany

[73] Assignee: Huels Aktiengesellschaft, Marl, Germany

[21] Appl. No.: 132,905

[22] Filed: Oct. 7, 1993

[30] Foreign Application Priority Data

Oct. 21, 1992 [DE] Germany .................. 4235431

[51] Int. Cl.$^6$ .................. C07C 7/00; B01D 3/00; B01D 3/42
[52] U.S. Cl. .................. 585/800; 203/26; 203/2; 203/3; 203/DIG. 4
[58] Field of Search .................. 585/800; 203/26, 2, 203/3, DIG. 4

[56] References Cited

U.S. PATENT DOCUMENTS 4,615,769  10/1986  Horigome et al. .................. 203/2

Primary Examiner—Helen M. S. Sneed
Assistant Examiner—Nhat D. Phan
Attorney, Agent, or Firm—Oblon, Spivak, McClelland, Maier & Neustadt

[57] ABSTRACT

A process for separating ethylbenzene and styrene by distillation is described. The process provides the advantages of a vapor compression/heat pump system, and is designed in such a manner that the energy applied is optimally utilized. The head pressure of the distillation column (1) is controlled in a simple manner, whereby a surprisingly stable column is achieved.

19 Claims, 1 Drawing Sheet

PROCESS FOR SEPARATING ETHYLBENZENE AND STYRENE BY DISTILLATION

BACKGROUND OF THE INVENTION

1. Field of the Invention

The present invention relates to a process for the separation of ethylbenzene and styrene by distillation. More particularly, it is drawn to the recovery of ethylbenzene and styrene from the crude product resulting from ethylbenzene dehydrogenation, utilizing the advantages of heat pump/vapor compression in a distillation process.

2. Discussion of the Background

Styrene is by far the most commercially important unsaturated aromatic monomer (see *Kirk-Othmer Encyclopedia of Chemical Technology*, Vol. 21, Third Edition (1983) pp. 770–801, incorporated by reference). The dominant manufacturing technique is the dehydrogenation of ethylbenzene, which provides a crude product composed mainly of styrene and ethylbenzene. Separation of this crude product by distillation is difficult because of the similar boiling points of styrene and ethylbenzene. Distillation is further complicated by the presence of impurities such as toluene, benzene, water, and nitrogen-containing species, and by practices such as the addition of vinyl aromatic polymerization inhibitors.

A great many distillation systems are known (see *ibid*, Vol. 7, pp. 849–891; *ibid*, Supplement, pp. 806–845; King, C. J., *Separation Processes*, Second Edition, McGraw-Hill, N.Y., 1980; incorporated by reference). Since the separation of ethylbenzene and styrene is both uniquely difficult and is of great economic importance, many distillation processes have been proposed specifically therefore. Such a process is disclosed, for example, in Bulletin VT 1673/74, May 1982, page 3, 12.4.1, Separation of Ethylbenzene/Styrene, Sulzer Company. However, control of the distillation column (crude styrene column) is not disclosed.

EP-B 0 160 553 teaches a further development of the process of the Sulzer Company. In this case, the vapor of the low boilers, including ethylbenzene, is withdrawn from the head of a distillation column and divided into two parts or streams. A first stream is passed in a known manner through a "preheater" in which the stream is superheated and then to a compressor for adiabatic compression. A second stream is passed to a condenser. The heat of condensation of the second stream is apparently lost to the system in the condenser, and the distillation column is controlled in a complicated manner. Although the distillation is highly stable (e.g. mass transfer is maintained at a constant rate and purity), it is costly.

Thus, there is a need for an efficient process of separating a mixture comprising ethylbenzene and styrene that is stable, easily controlled, and yet less costly.

SUMMARY OF THE INVENTION

Accordingly, one object of the present invention is to provide a process for separating ethylbenzene and styrene by distillation of a liquid mixture comprising styrene and ethylbenzene, which provides better energy utilization than the processes of the prior art.

A second object is to provide a distillation process in which mass transfer is maintained at a desired rate while the crude styrene column is controlled in the simplest possible manner.

BRIEF DESCRIPTION OF THE DRAWINGS

A more complete appreciation of the foregoing and other objects, features and advantages of the present invention will be readily obtained as the same becomes better understood by reference to the following detailed description when considered in connection with the accompanying drawing, wherein.

DESCRIPTION OF THE PREFERRED EMBODIMENTS

Figure 1:
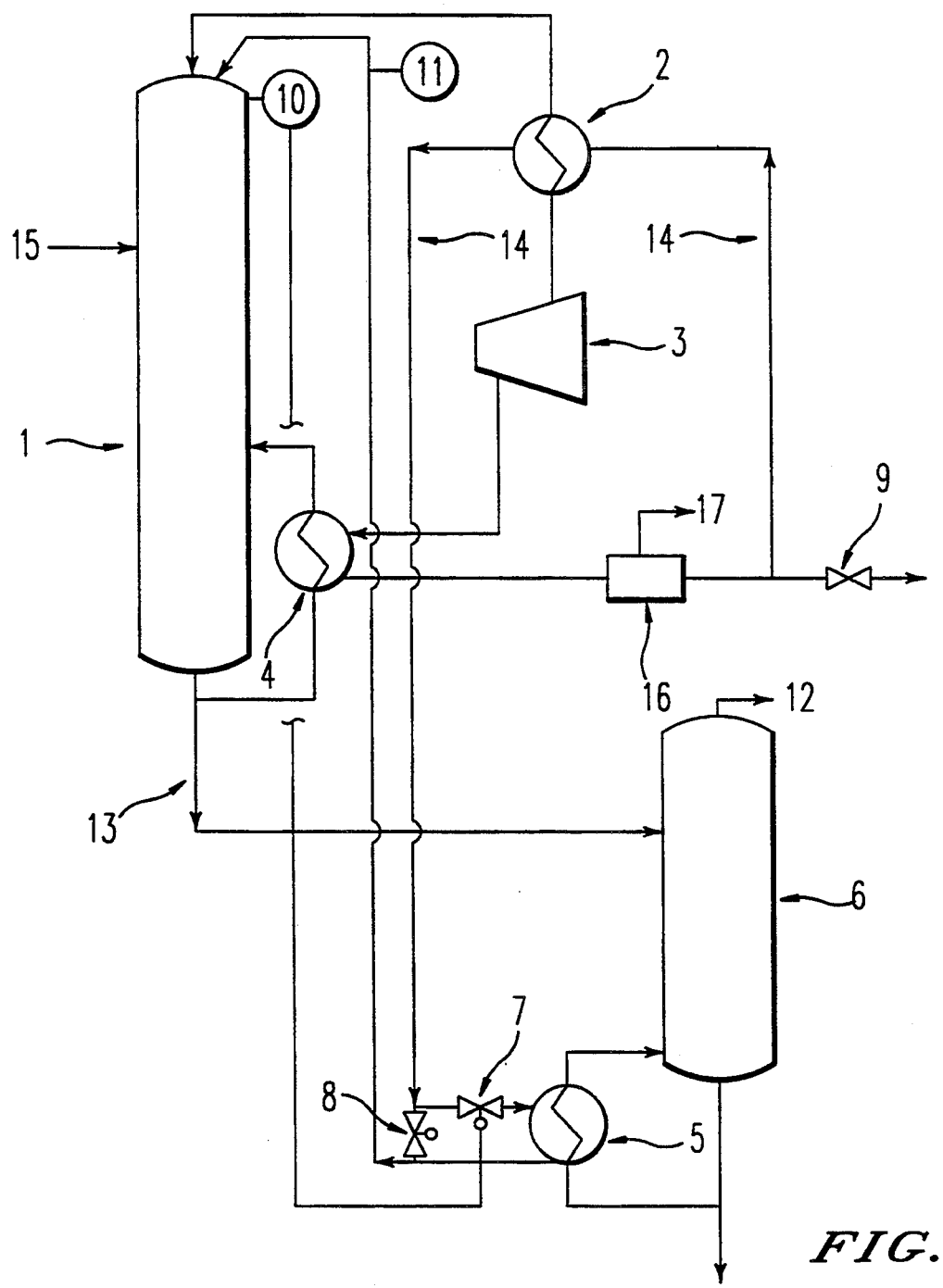
FIG. 1 is a schematic representation of the distillation process of the present invention.

Referring now to the drawings, wherein like reference numerals designate identical or corresponding parts, the process of the invention includes the following steps:

(a) feeding a liquid mixture comprising styrene and ethylbenzene (15) into a central part of a distillation column (1) (crude styrene column), preferably of the packed column type and preferably operated at reduced pressure;

(b) withdrawing the vapor of components having low boiling points (low boilers) with ethylbenzene from the head of the column (1) and withdrawing a liquid of components having high boiling points (high boilers) with styrene from the bottom part of the column (1);

(c) passing the vapor of the low boilers from the head of column (1), preferably first through a superheater (2), and then to a compressor (3) for adiabatic compression (vapor compression);

(d) introducing compressed vapor from the compressor (3) into a reboiler (4) of the column (1) to act as a heat source for the crude styrene column;

(e) recycling a part, or first stream, (14) of the liquid condensed in the reboiler (4) composed of low boilers, preferably again through the superheater (2), and withdrawing the remaining part, or second stream, of the condensed liquid composed of low boilers from the distillation system through outlet valve (9), wherein the part (14) of the condensed liquid composed of low boilers leaving the superheater (2) is further divided into two parts, or streams A and B, such that:

the first part, or stream A, is passed through valve (7) through a reboiler (5) of the distillation column (6) (pure styrene column), and the second part, or stream B, is passed through valve (8). The two parts then join and pass together to the upper part of column (1) as reflux. The first part passing through valve (7) thus acts as a heat source for the pure styrene column (6). The first part passing through valve (7) can alternatively be passed to another utilizable heat sink of appropriate temperature and then recycled to the upper part of the column (1).

Valves (7) and (8) may preferably be in a control circuit with a pressure measurement point (10) provided at or near the head of the column (1), designated by dotted lines in FIG. 1. The column (1) can then be operated by this control circuit. Surprisingly, such a control circuit allows a particularly stable condition of the column (1) to be achieved, by attenuation of mass transfer through valves (7) and (8) in conjunction with measurement of pressure at or near the head of column (1).

In another advantageous embodiment, styrene is separated off from higher boiling components by distillation over the head (12) of pure styrene column (6). Column (6) is preferably of the packed column type and preferably operated at reduced pressure. It is fed at a central part of the column with the liquid composed of high boilers from the bottom part of column (1).

The location of the vacuum source, if provided, is not particularly critical. However, in an advantageous embodiment, the distillation process further comprises passing the low boilers from reboiler (4) into a condenser or distillate receiver (16). Additional condensation of low boilers may occur in this distillate receiver. In this case, the vacuum supply (17) may be connected through distillate receiver (16).

The liquid mixture comprising styrene and ethylbenzene can be the crude product from the dehydrogenation of ethylbenzene, in which case it is predominantly composed of these two compounds. It also generally contains toluene, benzene, and substances such as nitrogen-containing species and water.

In still another advantageous embodiment, the crude product from the dehydrogenation of ethylbenzene can be first fed to a different distillation column from which toluene, benzene, low-boiling nitrogen-containing species and water are withdrawn via the head. A mixture is then withdrawn from the bottom part of the column which is essentially composed of styrene and ethylbenzene (bottoms product). This mixture becomes the feed (15) for the distillation column (1).

The line for the two combined parts leaving valves (7) and (8) (the reflux line), preferably contains a measurement point (11) for the measurement of the reflux rate. In this preferred embodiment, it is further preferred that the compressor (3) be equipped with an apparatus for setting the output, e.g. an inlet guide vane. The output of the compressor is then integrated into a control circuit with the measurement taken at measurement point (11). The reflux rate is thus controlled by the output of the compressor. This allows an even finer control of mass transfer throughout the distillation system when integrated with the pressure measurement point (10) control circuit previously mentioned. The control circuits involving measurement points (10) and (11) are thus combined in a single control circuit, so that the compressor and valves (7) and (8) are controlled simultaneously by two measurement points.

In addition, temperature measurement points can be preferably situated in a central part of the column (1). The temperature measurement points and valve (9) may also be integrated in a control circuit. This control circuit may further be integrated with one or both of the aforementioned control Circuits. This provides a still more accurate means of control of mass transfer throughout the entire system by attenuating of the amount of low boilers withdrawn from the distillation system.

The composition of the product streams leaving the distillation system of column (1), that is the liquid product stream composed of low boilers and the liquid product stream composed of high boilers, is preferably continuously determined by gas chromatography. Likewise, the liquid feed (15) composition is preferably continuously determined by gas chromatography.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for separating ethylbenzene and styrene comprising:
   (a) feeding a mixture including ethylbenzene and styrene to a distillation system comprising a first distillation column having a reboiler;
   (b) withdrawing low boilers comprising ethylbenzene from a top part of the first distillation column and high boilers comprising styrene from a bottom part of the distillation column;
   (c) passing the high boilers to a second distillation column having a reboiler;
   (d) passing the low boilers to a compressor and then through the reboiler of the first distillation column, whereby at least a portion of the low boilers pass from a vapor to a liquid;
   (e) dividing the liquid into a first part and a second part, the first part being withdrawn through an outlet valve and out of the distillation system, and the second part being divided into two streams, whereby:
   the first stream passes through a first valve to a reflux line,
   and the second stream passes through a second valve, through a heat sink, and then the second stream is passed to the reflux line,
   said reflux line then returning the two streams to the first distillation column.

2. The process according to claim 1, wherein the heat sink is the reboiler of the second distillation column.

3. The process according to claim 1, wherein after the low boilers pass through the reboiler of the first distillation column, the low boilers pass through a condenser, said condenser being connected to a vacuum means.

4. The process according to claim 1, wherein said first and second valves are controlled by a pressure measurement means of said first distillation column.

5. The process according to claim 1, wherein said outlet valve is controlled by a temperature measurement means of said first distillation column.

6. The process according to claim 1, wherein a reflux rate measurement means of the reflux line controls the output of the compressor.

7. The process according to claim 1, wherein the composition of the high boilers leaving the first distillation column is determined by gas chromatography.

8. The process according to claim 1, wherein the composition of the low boilers leaving the first distillation column is determined by gas chromatography.

9. The process according to claim 1, wherein said mixture fed into the distillation system is the crude product of ethylbenzene dehydrogenation.

10. A process for separating ethylbenzene and styrene by distillation of a liquid mixture including styrene and ethylbenzene, comprising:
   (a) feeding the liquid mixture into a central part of a first distillation column having a head and a bottom part;
   (b) withdrawing low boilers comprising ethylbenzene from the head of the first distillation column and withdrawing a liquid comprising styrene from the bottom part of the first distillation column;
   (c) passing the low boilers comprising ethylbenzene through a superheater to a compressor for adiabatic compression;

(d) passing the adiabatically compressed low boilers comprising ethylbenzene into a reboiler of the first distillation column;

(e) dividing the low boilers leaving the reboiler of the first distillation column into two parts, recycling a part by passing it through a superheater to an upper part of the first distillation column and withdrawing the remaining part from the distillation system;

wherein the part passing through a superheater is divided into two streams, A and B, such that:

stream A is passed through a heat sink and then passed to a reflux line, and stream B is passed directly to the reflux line.

11. The process according to claim 10, wherein the liquid comprising styrene withdrawn from the bottom part of the first distillation column is passed to a second distillation column having a head and bottom part and a reboiler, wherein styrene is separated from higher boiling components by distillation over the head of the second distillation column.

12. The process according to claim 11, wherein the heat sink through which the first stream passes is the reboiler of the second distillation column.

13. The process according to claim 10, wherein the head of the first distillation column further comprises a pressure measurement means, stream A passes through a first valve, and stream B passes through a second valve, and wherein the valves are controlled by the pressure measurement means.

14. The process according to claim 10, wherein a measurement point for the measurement of the reflux rate is situated in a line for the combined streams A and B, and the compressor is equipped with an apparatus for setting the output, where the reflux rate is set by the output.

15. The process according to claim 10, wherein at least one temperature measurement point is situated in a central part of the first distillation column and a valve is situated in the line for withdrawing the remaining part of the low boilers leaving the reboiler of the first distillation column from the distillation system, where the temperature measurement and the valve are in a control circuit.

16. A process according to claim 10, wherein the low boilers leaving the reboiler of the first distillation column are passed into a condenser which is connected to a vacuum unit.

17. The process according to claim 10, wherein the liquid mixture fed into the central part of the first distillation column is the crude product from the dehydrogenation of ethylbenzene.

18. The process according to claim 17, wherein the crude product from the dehydrogenation of ethylbenzene is first fed to a different distillation column, and wherein the liquid mixture fed into the central part of the first distillation column is a bottoms product of the different distillation column.

19. The process according to claim 10, wherein the reflux line contains a means for the measurement of the reflux rate, and wherein said means is in control circuit whereby the reflux rate is controlled.

* * * * *